United States Patent [19]

Finkel

[11] Patent Number: 4,469,491
[45] Date of Patent: Sep. 4, 1984

[54] SEPARATION OF DIISOPROPYLETHER FROM HYDROCARBON STREAMS

[75] Inventor: Lawrence H. Finkel, Wayne, Pa.

[73] Assignee: Sun Tech, Inc., Philadelphia, Pa.

[21] Appl. No.: 369,961

[22] Filed: Apr. 19, 1982

[51] Int. Cl.³ .................. B01D 3/40; B01D 53/14; C07C 7/11
[52] U.S. Cl. .......................... 55/29; 55/84; 203/18; 203/42; 203/64; 203/88; 568/699; 568/896; 585/864
[58] Field of Search .............. 203/64, 88, 42-46, 203/80, 14, 18; 55/84, 85, 89; 568/694-696, 699, 895-901; 585/864

[56] References Cited

U.S. PATENT DOCUMENTS

| | | | |
|---|---|---|---|
| 1,442,520 | 1/1923 | Buc | 568/699 |
| 1,536,544 | 5/1925 | Willkie | 568/699 |
| 1,974,069 | 9/1934 | Greer | 203/64 X |
| 2,273,923 | 2/1942 | Bludworth | 203/64 |
| 2,927,064 | 1/1960 | Luzader et al. | 203/64 X |
| 3,410,762 | 11/1968 | Dean | 203/64 |
| 3,464,896 | 9/1969 | Washall | 203/64 X |
| 3,578,568 | 5/1971 | Washall | 203/64 |
| 4,218,569 | 8/1980 | Chase et al. | 568/699 X |
| 4,237,325 | 12/1980 | Brandes et al. | 568/896 |
| 4,322,565 | 3/1982 | Dotson et al. | 568/699 X |

Primary Examiner—Wilbur L. Bascomb, Jr.
Attorney, Agent, or Firm—J. Edward Hess; Donald R. Johnson

[57] ABSTRACT

A process for the separation of diisopropylether from a hydrocarbon stream containing it, by contacting the stream with ethylene glycol whereby the diisopropylether is absorbed by the glycol and a purified hydrocarbon stream is separated therefrom.

5 Claims, 1 Drawing Figure

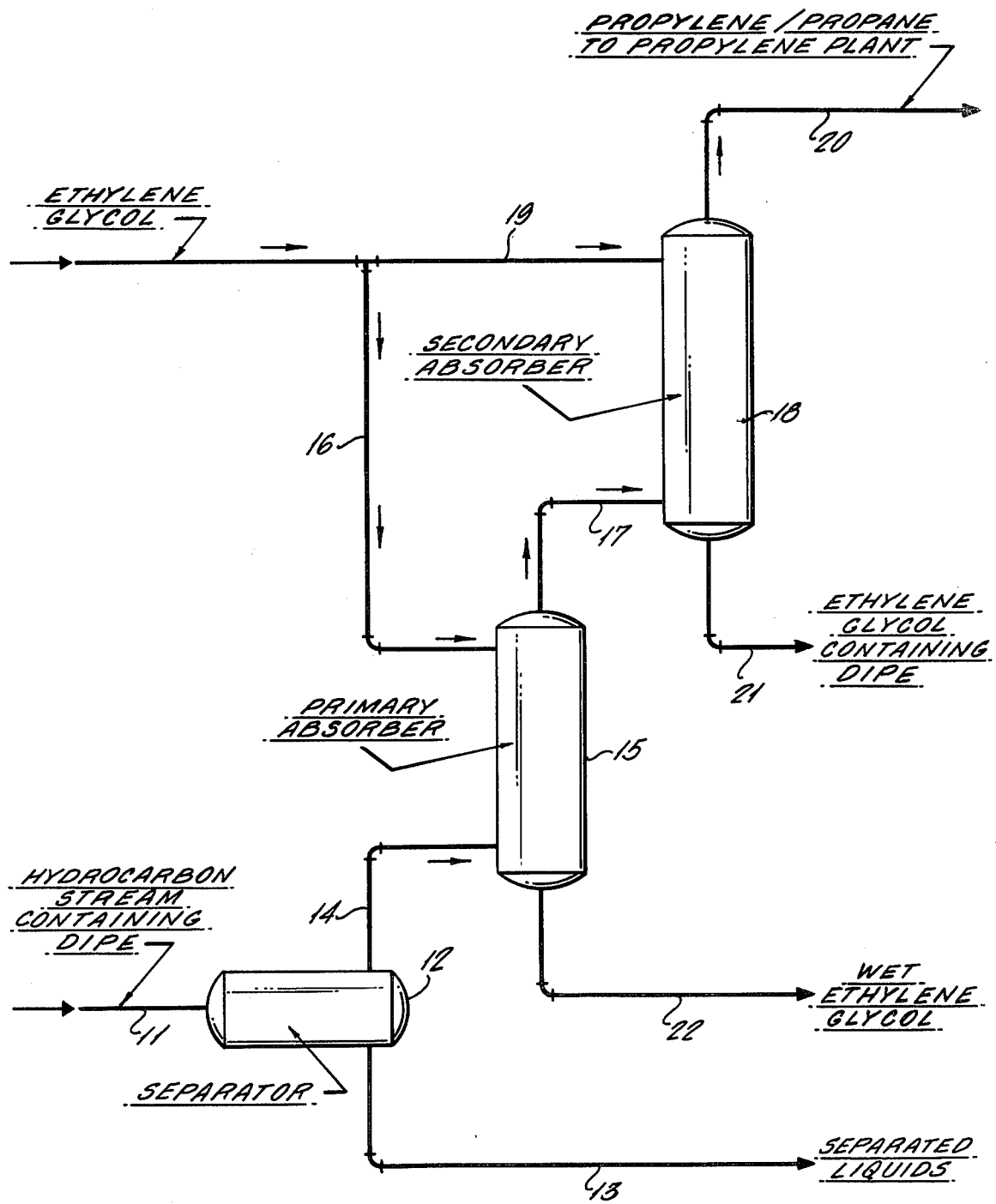

SEPARATION OF DIISOPROPYLETHER FROM HYDROCARBON STREAMS

This invention relates to a method for removing diisopropylether from its admixture with a hydrocarbon. More particularly, the invention provides a process from removing diisopropylether from chemical or refinery process streams of propane, propylene and their admixture.

BACKGROUND OF THE INVENTION

When propylene, which usually contains some propane, is catalytically hydrated to form isopropanol (IPA), by-product diisopropylether (DIPE) is formed. The propane and unreacted propylene are valuable materials which are further processed for recovery, but the presence of the DIPE is a problem as it can form peroxides which are potentially explosive. Thus, there is a need to efficiently and effectively remove the DIPE from the hydrocarbon process stream.

It is known in the prior art from the disclosure of U.S. Pat. No. 1,974,069 that ethyl ether can be dried by contact with ethylene glycol which removes the water and then the dry ether product is subsequently distilled off. This, of course, is contrary to applicant's process where the glycol is used to remove an ether. Also of interest is U.S. Pat. No. 3,410,762 which discloses the separation of ethers from high boiling residues by subjecting the residues to azeotropic distillation with a diol of 2 to 4 carbon atoms. U.S. Pat. No. 3,578,568 discloses the extractive distillation of $C_3$ to $C_5$ monoepoxides with glycols, such as ethylene glycol, or their ethers whereby oxygen containing compounds such as water, methanol, acetaldehyde, acetone and the like are and removed from the epoxide. In U.S. Pat. No. 2,927,064 an aromatic ether, alpha-methylbenzyl ether, is purified by azeotropic distillation of the ether with ethylene glycol.

BRIEF STATEMENT OF THE INVENTION

A novel, effective process for removing diisopropylether (DIPE) from its admixture with a hydrocarbon, particularly a $C_3$-hydrocarbon, is provided by contacting the ether-containing hydrocarbon with ethylene glycol whereby the undesired ether is absorbed by the glycol. In a more particular embodiment, a $C_3$-hydrocarbon stream containing DIPE is subjected to counter current extraction with ethylene glycol to remove the ether. In a further embodiment, the inventions relates to the process of catalytically hydrating a propylene stream to isopropanol wherein water is subsequently separated from the isopropanol product by extractive distillation with ethylene glycol and provides the improvement of removing diisopropylether by-product formed in said hydration step and carried over into the stream of unreacted propylene separated from said hydration step by contacting said diisopropylether containing stream with ethylene glycol whereby said diisopropylether is absorbed. The drawing illustrates the separation of diisopropylether from a hydrocarbon stream by extraction with ethylene glycol according to the process of the invention.

DETAILED DESCRIPTION OF THE INVENTION

In order to illustrate the invention the discussion which follows will relate to the separation of DIPE from a $C_3$-hydrocarbon stream comprised of unreacted propylene and propane obtained from the catalytic hydration of a propylene stream containing some propane. However, it will be understood that the invention applies to the separation of DIPE from hydrocarbon streams generally.

As indicated above, in the direct hydration of propylene contained in a stream containing propylene and propane, by product diisopropylether is formed along with the primary isopropyl alcohol product. The unreacted propylene along with the inert propane that accompanies the feed propylene may readily be separated from the reaction mixture of water, isopropyl alcohol (IPA) and DIPE by simple flash distillation.

However, when the propylene-propane gas stream is separated from the IPA, equilibrium concentrations of DIPE, IPA and water are carried in it. To avoid the presence of DIPE in the propane when it is separated from propylene by fractionation to make LPG, the aforementioned propylene-propane stream is countercurrently contacted with ethylene glycol.

Since the absorber operation causes water and some IPA to be adsorbed into ethylene glycol in addition to the DIPE, it is preferred to perform two absorptions in sequence in order isolate water-containing ethylene glycol.

In the drawing, the hydrocarbon stream shown as line 11 enters a flash separator 12 operated at about 330 pounds pressure where liquid comprising water, IPA, and much of the DIPE present is removed as bottoms through line 13 and the gaseous DIPE-containing stream passes overhead through line 14 to the lower end of a primary absorber 15. Ethylene glycol at an elevated temperature of from about 100° to about 400° F. (preferably about 285° F.) from line 16 enters an area near the top of the primary absorber 15 at a minimum rate of about 45 pound moles per hour and extraction occurs in the absorber whereby water-wet ethylene glycol is removed from the absorber bottom at line 22. The partially extracted stream is taken overhead through line 17 to the lower end of the secondary absorber 18 where ethylene glycol from line 19 at a temperature of from about 100° to about 300° F. (preferably about 175° F.) enters near the top at a rate of between about 50 and about 900 pound moles per hour (preferably at about 900 pound moles per hour) and further extraction occurs. The overhead DIPE-free stream is taken through line 20 to further processing and the DIPE-containing ethylene glycol is taken from the bottom of the absorber through line 21. It will be understood that the temperature, rates of flow, number of theoretical stages, and the like will be adjusted to achieve the desired level of absorption of the diisopropylether. In carrying out the process of this invention on a commercial scale, the parameters set forth above will enable a stream of $C_3$-hydrocarbons to be obtained containing less than 50 ppb of diisopropylether.

The selectivity for these constituents in a typical run in a single absorption is shown by the following absorber balance, using 3 theoretical stages.

| Components | Line 11 Incoming | Line 17 Exiting |
|---|---|---|
| Propylene | 535.7 | 535.6 |
| Propane | 322.5 | 322.5 |
| DIPE | 10.3 | 7.2 |
| IPA | 36.2 | 15.9 |
| Water | 16.5 | 1.5 |

-continued

| Components | Line 11 Incoming | Line 17 Exiting |
|---|---|---|
| Ethylene Glycol | 0.0 | 1.1 |
| Total (lb moles/hr) | 921.2 | 883.8 |
| (°F., PSIG) | (170,330) | (202,325) |
| Glycol Flow In | 47.0 | |

Alternately, by using 15 theoretical stages and 210 moles/hr of fresh glycol, essentially all of the water and 99% of the IPE in the incoming propylene/propane gas is removed in a single treatment.

In a commercial operation based on the details shown in the drawing, the initial absorber extracts at least 90% of the initial water vapor in the incoming gas. The amount of water-containing glycol is small relative to the glycol used in the secondary absorber. The scrubbed gas goes on to the secondary absorber where the IPE content is readily reduced to less than 50 ppb using appropriate glycol quantities and theoretical stages. The overall balance shown above applies to the primary (small) absorber. The following table shows the effectiveness of the extraction in the secondary absorber:

| Components | Gas From 1st Absorber | Gas From 2nd Absorber |
|---|---|---|
| Propylene | 535.6 | 535.5 |
| Propane | 322.5 | 322.3 |
| DIPE | 7.2 | 0.0 |
| IPA | 15.9 | 0.0 |
| $H_2O$ | 1.5 | 0.01 |
| Ethylene Glycol | 1.1 | 0.6 |
| Total | 883.8 | 858.4 |
| Glycol Flow In | | 900.0 |

In a particular and preferred embodiment of the invention the ethylene glycol used for the extraction process of this invention may be integrated with the extractive distillation step used to separate water from the isopropanol product obtained by the propylene hydration. The extractive distillation is carried out by contacting the IPA-water mixture in a fractional distillation zone with ethylene glycol at distillation temperature as disclosed in U.S. Pat. No. 3,464,896 which disclosure is hereby incorporated by reference. In a preferred embodiment of this invention the ethylene glycol recycle stream used for the extractive distillation will feed both the extractive distillation and the primary and secondary absorbers used in the process of this invention and also the wet ethylene glycol stream from the primary absorber (line 22) and the essentially dry ethylene glycol stream from the secondary absorber (line 21) will be used as a partial feed to the extractive distillation step.

I claim:

1. A process for the separation of diisopropylether from a hydrocarbon stream containing it, which comprises contacting said stream with ethylene glycol whereby said diisopropylether is absorbed by said glycol and a purified hydrocarbon stream is separated therefrom.

2. The process of claim 1 wherein said hydrocarbon stream is a $C_3$-hydrocarbon stream.

3. The process of claim 2 wherein the hydrocarbon stream comprises propylene.

4. The process of claim 3 wherein the diisopropylether is a by-product obtained in a previous reaction of propylene with water to form isopropyl alcohol, and the propylene is unreacted propylene from said previous reaction.

5. Process for removing diisopropylether and water from a propylene stream removed as unreacted propylene from a previous hydration of propylene to isopropyl alcohol which comprises contacting said stream with ethylene glycol in a first absorption zone, removing from said first absorption zone an ethylene glycol stream containing water removed from said propylene stream and a treated propylene stream containing diisopropylether, contacting said treated propylene stream with ethylene glycol in a second absorption zone, removing from said second absorption zone an ethylene glycol stream containing diisopropylether removed from said treated propylene stream and a further treated propylene stream from which diisopropylether and water have been removed.

* * * * *

UNITED STATES PATENT AND TRADEMARK OFFICE
CERTIFICATE OF CORRECTION

PATENT NO. : 4,469,491

DATED : September 4, 1984

INVENTOR(S) : Lawrence H. Finkel

It is certified that error appears in the above-identified patent and that said Letters Patent is hereby corrected as shown below:

Column 3, line 11, "IPE" should read -- DIPE --.

Column 3, line 19, "IPE" should read -- DIPE --.

Signed and Sealed this

Twelfth Day of March 1985

[SEAL]

Attest:

DONALD J. QUIGG

Attesting Officer    Acting Commissioner of Patents and Trademarks